United States Patent [19]
Tom

[11] Patent Number: 6,156,578
[45] Date of Patent: Dec. 5, 2000

[54] QUARTZ CRYSTAL MICROBALANCE SYSTEM FOR DETECTING CONCENTRATION OF A SELECTED GAS COMPONENT IN A MULTICOMPONENT GAS STREAM

[75] Inventor: Glenn M. Tom, New Milford, Conn.

[73] Assignee: Advanced Technology Materials, Inc., Danbury, Conn.

[21] Appl. No.: 09/088,315

[22] Filed: Jun. 1, 1998

[51] Int. Cl.[7] .......................... G01N 27/04; G01N 29/02
[52] U.S. Cl. ............................ 436/149; 436/55; 422/90; 422/62; 73/24.06
[58] Field of Search .................. 422/83, 88, 90, 422/62; 436/148, 149, 151, 55; 73/24.01, 24.05, 24.06, 579

[56] References Cited

U.S. PATENT DOCUMENTS

| | | |
|---|---|---|
| Re. 35,544 | 7/1997 | Snow . |
| 3,744,296 | 7/1973 | Beltzer . |
| 4,056,803 | 11/1977 | White et al. . |
| 4,163,384 | 8/1979 | Blakemore . |
| 4,399,686 | 8/1983 | Kindlund et al. . |
| 4,446,720 | 5/1984 | Sinclair . |
| 4,637,987 | 1/1987 | Minten et al. . |
| 4,730,478 | 3/1988 | Gedeon . |
| 4,735,081 | 4/1988 | Luoma et al. . |
| 5,037,624 | 8/1991 | Tom et al. . |
| 5,042,288 | 8/1991 | Vig . |
| 5,056,355 | 10/1991 | Hepher . |
| 5,065,140 | 11/1991 | Neuberger . |
| 5,095,736 | 3/1992 | Fesler et al. . |
| 5,138,869 | 8/1992 | Tom . |
| 5,151,110 | 9/1992 | Bein et al. . |
| 5,151,395 | 9/1992 | Tom . |
| 5,320,817 | 6/1994 | Hardwick et al. . |
| 5,325,705 | 7/1994 | Tom . |
| 5,339,675 | 8/1994 | DiLeo et al. . |
| 5,385,689 | 1/1995 | Tom et al. ............................. 252/194 |
| 5,411,709 | 5/1995 | Furuki et al. . |
| 5,417,821 | 5/1995 | Pyke . |
| 5,445,008 | 8/1995 | Watcher et al. . |
| 5,476,002 | 12/1995 | Bowers et al. . |
| 5,518,528 | 5/1996 | Tom et al. . |
| 5,573,728 | 11/1996 | Loesch et al. . |
| 5,661,226 | 8/1997 | Bowers et al. . |
| 5,705,399 | 1/1998 | Larue . |
| 5,756,631 | 5/1998 | Grate ........................................ 422/83 |
| 5,827,947 | 10/1998 | Miller et al. ........................ 73/24.06 |
| 5,866,798 | 2/1999 | Schonfeld et al. ................... 73/24.06 |

OTHER PUBLICATIONS

Karter, L., "NASA Proposes Zeolite Coats for Contamination Monitoring", *NASA Tech. Briefs*, Nov. 96.

Neuburger, Glen G., "Detection of Ambient Hydrogen Chloride with a Zinc–Coated Piezoelectric Crystal Resonator Operating in a Frequency–Time Different Mode," *Anal. Chem.* 1989, vol. 61, pp. 1559–1563.

Levenson, Leonard, L., "II. Chemisorption on Single Element Thin Films," in *Applications of Piezoelectric Quartz Crystal Microbalances*, C.Lu, editor, vol. 7, Elsevier, Amsterdam, 1984, pp. 198–203.

"The Worlds First 8–Bit RISC MCU in an 8–Pin Package," Philips Semiconductors, Nov. 7, 1997, 12 pages.

"SA612A Double–Balanced Mixer and Oscillator," Philips Semiconductors, Nov. 7, 1997, 12 pages.

*Primary Examiner*—Robert J. Warden, Sr.
*Assistant Examiner*—Andrew Aldag
*Attorney, Agent, or Firm*—Steven J. Hultquist; William A. Barrett; Oliver A.M. Zitzmann

[57] ABSTRACT

A quartz microbalance detector system for controlling the concentration of a gas component in a gas stream. The quartz microbalance interacts with the gas component, to effect a change in the oscillation frequency of the quartz microbalance detector and produce a signal correlative of concentration of the gas component in the gas stream. A specific embodiment includes a device for sensing concentration of a halogen-containing gas species in a gas stream, comprising a quartz microbalance detector having a quartz crystal with a surface functionalized with —OH functionality that reversibly reacts with the gas component to yield a bound reaction product on the surface that effects a change in the oscillation frequency of the quartz microbalance detector. The quartz microbalance may be utilized to maintain a set-point concentration of a gas compound in a multicomponent stream.

47 Claims, 10 Drawing Sheets

QUARTZ CRYSTAL MICROBALANCE SYSTEM FOR DETECTING CONCENTRATION OF A SELECTED GAS COMPONENT IN A MULTICOMPONENT GAS STREAM

BACKGROUND OF THE INVENTION

1. Field of the Invention

This invention relates generally to quartz crystal microbalance systems, and to a process and apparatus for delivery of a product gas stream containing a desired concentration level of a specific gas component.

2. Description of the Related Art

In many applications and industrial processes, there is need to deliver a multicomponent gas stream as a product containing a particular concentration of a specific gas component.

One such field is semiconductor manufacturing, in which the product gas stream may include one or more reagents, either with or without a carrier gas, for vapor deposition processes in a deposition chamber. The deposition process may be carried out to form a layer or structure in which the thickness and composition of the deposited material is critical to the operability and function of the resulting product device. Particularly when multicomponent deposition operations are being conducted, and stoichiometry of the deposited film is critical, the concentration of specific components in the product gas stream requires control within strict tolerances to meet process objectives.

A specific example in semiconductor manufacturing is trichlorosilane delivery from bubbler systems for formation of silicon and/or silicon oxides. In conventional trichlorosilane bubbler delivery systems, the variation in film thickness of the silicon-containing material is on the order of 5%–10% across the surface of the film. Such thickness variation is unacceptable for many applications.

Specifically, this level of thickness variability may necessitate the rejection of significant amounts of product articles, due to cumulation of the thickness variation through the succeeding material layers deposited on the silicon-containing material. Additionally, or alternatively, such variation in thickness may require remedial treatment to planarize or otherwise compensate for the variation in the applied film thickness.

The measure of the effectiveness of the control on the deposition process includes a number of measurement parameters. Illustrative parameters include accuracy, precision and resolution. Accuracy is a measure of how close a measured value is to the actual value, and is an important factor in the measurements used in process control. Precision is a measure of the reproducibility of the measurement. The precision measurement may have span or offset errors but the measurement and the process can still remain reproducible. Resolution is the ability to divide the measurement into fine segments of the whole.

These illustrative parameters can be expressed as bit values. A bit value is 2 to the bit power. For example, 8-bit is $2^8$ or 256. A semiconductor manufacturing process capable of achieving 9-bit precision would significantly improve the control and resulting quality of the deposition process and the product.

For example, in order to achieve 9-bit precision or accuracy, an instrument must be capable of resolving one part in 512, or 0.2%. Resolution of one part in 512 achieves 9-bit precision, if the results are reproducible. With no span or offset errors, 9-bit resolution and 9-bit precision results in 9-bit accuracy.

Drift or span or offset will degrade accuracy but will not necessarily degrade precision. Further, if the drift is slow on the time scale of a process being controlled, such as a wafer run, then the loss of accuracy may not be a significant impediment to control of the deposition process.

If the concentration or partial pressure of a process chemical such as TCS could be accurately, precisely and reproducibly measured, then a feedback loop control system could be utilized to maintain the flux of the process chemical into the tool at a higher level or accuracy and precision than heretofore possible.

Quartz microbalance systems are known in the art for monitoring gas concentrations.

One such system for monitoring components of a fluid or gaseous mixture is disclosed in U.S. patent application Ser. No. 08/785,342 filed Jan. 17, 1997 (now U.S. Pat. No. 5,827,947) in the names of Cynthia A. Miller and Glenn M. Tom for "Piezoelectric Sensor for Hydride Gases, and Fluid Monitoring Apparatus Comprising Same," the specification of which is hereby incorporated herein by reference in its entirely.

Other quartz microbalance systems are described in U.S. Pat. No. 4,637,987 to Minten et al. and U.S. Pat. No. 5,065,140 to G. G. Neuberger.

In quartz microbalance gas detection systems, a quartz crystal element with one or more specialized coatings on the crystal may be utilized to monitor gas concentration. The crystal is oscillated by an electric field at a frequency determined by the mass of the crystal. Any change in crystal mass will result in a change in the oscillation frequency. As the coating adsorbs or reacts with specific gas constituents, the mass of the crystal will change.

The oscillation frequency of the quartz crystal may therefore be monitored to determine gas concentration, taking advantage of the fact that when the mass of the crystal increases, the oscillation frequency will decrease, thereby indicating an increase in the concentration of a specific gas constituent.

Accordingly, it would be a significant advance in the art, and accordingly is an object of the present invention, to provide a gas stream supply system in which TCS or other component is supplied to a semiconductor manufacturing deposition process at a precise concentration in the delivered gas stream, so that the resulting deposited thickness of the material deposited from such stream is highly uniform in character.

It is another object of the invention to provide a quartz microbalance sensor of high resolution characteristics for detection and measurement of gas concentration in such applications.

It is yet another object of the present invention to provide a control system for delivery of a gas component of a multicomponent gas stream at a selected concentration with a low level of variance in the gas concentration.

It is another object of the present invention to provide a highly efficient detector for determining the concentration of a selected component in a multicomponent gas stream.

Other objects and advantages of the invention will be more fully apparent from the ensuing disclosure and appended claims.

SUMMARY OF THE INVENTION

The present invention relates in a broad aspect to a device for sensing concentration of a gas component in a gas stream, comprising a quartz microbalance detector that interacts with the gas component to effect a change in the oscillation frequency of the quartz microbalance detector, with means for inputting electrical energy to the quartz microbalance detector and outputting therefrom a signal correlative of concentration of the gas component in the gas stream.

In accordance with one aspect of the invention, the quartz microbalance detector includes a quartz crystal with a surface functionalized with hydroxyl functionality which reversibly reacts with the gas component to yield a surface-bound reaction product that (1) effects a change in the oscillation frequency of the quartz crystal and (2) is regenerable in the presence of water vapor to re-establish the hydroxyl functionality on such surface. The hydroxyl (—OH) functionality may be provided by a physical adsorbent species coated on the surface of the quartz crystal and including such hydroxyl functionality.

The hydroxyl functionality is reversibly reactive, and may be utilized for detection or monitoring of concentration of trichlorosilane or other halogen gas. For example, relative to trichlorosilane as the halogen gas species in the gas stream being monitored, and contacted with a quartz microbalance detector including a quartz crystal whose surface is functionalized with hydroxyl functionality, the halosilane will reactively bind to the oxo (—O—) moiety of the hydroxyl functionality, to yield bound halosiloxy groups on the quartz crystal surface that are reversibly bound to such surface.

If such halosiloxified surface is thereafter exposed to air containing relative humidity, the halosilyl component of the bound group is reactively liberated from the surface, to reestablish the surface hydroxyl functionality. This affords a methodology for regenerating the crystal after it is loaded with the halosilyl species, to repopulate the surface of the quartz crystal with —OH groups.

Since the quartz crystal microbalance is formed of silica, it will inherently have some native hydroxyl functionality. This native hydroxyl functionality may be selectively augmented in the practice of the present invention by coating the quartz crystal microbalance with a film of silanol or a metal hydroxide, to provide a suitable surface density of hydroxy groups. As a still further alternative, various organic coatings imparting hydroxyl functionality may be coated on the quartz microbalance surface, including polyvinylalcohol (PVA), dextrans, polystyrene divinylbenzene, or other hydroxy-functional organic coatings, carbonaceous waxes having hydroxyl functionality, and precursor functionalities (which in contact with the gas being detected are converted to hydroxy functionality, which then in turn reacts with the gas being monitored to yield a reversibly bound species indicative of the presence of the gas component of interest).

For example, in some instances involving monitoring of trichlorosilane, it may be feasible to provide a surface coating on the quartz microbalance of an alkoxide having alkoxy functionality, which in initial contact with trichlorosilane reacts to yield hydroxy functionality on the surface, which then reacts further to yield the reversibly bound species.

The coatings of the invention may be applied by sol gel or other coating techniques, as hereinafter more fully described. The physical adsorbent coating is desirably as thin as feasible, consistent with establishment of the continuous film on the surface. In general, the thinner the coating, the faster the response. In general, thicknesses are desired which are in the range of from about 0.1 micrometer to 100 micrometers, although any suitable thickness may be employed, consistent with the material being monitored, the specific composition of the coating, and the response characteristics desired.

The invention therefore contemplates the functionalization of the quartz microbalance surface with hydroxyl functionality with which trichlorosilane is reactive to produce a bound halosiloxy species. Such halosiloxy species then react upon exposure of the quartz microbalance surface to ambient air repopulate the coating with hydroxyl functionality. Such quartz microbalance in use is desirably maintained free of exposure to atmospheric gases and ambient moisture (relative to humidity). If the quartz microbalance system is maintained in an inactive (non-monitoring) state, it may for example be blanketed by argon or other inert gas to avoid the need for recalibration.

In one aspect the invention relates to a method of determining the concentration of a gas component in a gas mixture comprising same, wherein the gas component is reversibly reactive with hydroxyl functionality, and said hydroxyl functionality is regenerable in the presence of water vapor to re-establish the hydroxyl functionality, the method comprising the steps of:

providing a quartz crystal microbalance including a quartz crystal with a surface functionalized with hydroxyl functionality which reversibly reacts with the gas component to yield a surface-bound reaction product that (1) effects a change in the oscillation frequency of the quartz crystal and (2) subsequent to reaction is regenerable in the presence of water vapor to re-establish the hydroxyl functionality on said surface; and sensing the oscillation frequency of the quartz crystal and generating an output correlative of the concentration of the gas component in the gas stream.

Another aspect of the invention relates to a method of monitoring partial pressure or vapor pressure of a halofunctional gas in a bubbler, comprising the steps of:

providing a quartz crystal microbalance including a quartz crystal with a surface functionalized with silanol functionality which reversibly reacts with the halofunctionality of the gas component to yield a surface-bound reaction product which effects a change in the oscillation frequency of the quartz crystal;

sensing the oscillation frequency of the quartz crystal and generating an output correlative of the concentration of the halo-functional gas component in the gas stream; and converting such output to a value of the partial pressure or vapor pressure of the halo-functional gas in the bubbler.

In a further aspect the invention relates to a system for supplying a gas component in a gas stream to a delivery site at a set point concentration, comprising:

a gas stream flow circuit for flow of the gas stream therethrough to the delivery site;

means for introducing the gas component to the gas stream upstream of the delivery site at adjustably variable rate;

a quartz microbalance detector including a quartz crystal with a surface functionality that reversibly reacts with the gas component to form a bound reaction product on the surface and effects a change in the oscillation frequency of the quartz microbalance detector, with means for inputting electrical energy to the quartz crystal and outputting a detector signal therefrom that is correlative of concentration of the gas component in the gas stream; and means for processing said detector signal, responsively generating a control signal, and adjusting the gas component introducing means via the control signal to introduce the gas component to the gas stream in sufficient quantity and rate to yield the set point concentration of the gas component in the gas stream at the delivery site.

A still further aspect of the invention relates to a method of supplying to a delivery site a gas stream containing a gas component at a set point concentration, comprising the steps of:

flowing a source gas stream along a flow path to the delivery site;

adding the gas component to the source gas stream in the flow path upstream of the delivery site to form the gas stream delivered to the delivery site;

providing a quartz microbalance detector including a quartz crystal with a surface functionality that reversibly reacts with the gas component to form a reaction product bound to the surface that effects a change in the oscillation frequency of the quartz microbalance detector;

inputting electrical energy to the quartz microbalance detector and outputting a signal therefrom correlative of concentration of the gas component in the gas stream;

exposing at least a portion of the gas stream to the quartz microbalance detector to generate the correlative output signal therefrom;

controlling the amount of gas component that is added to the source gas stream to yield the gas stream flowed to the delivery site, in response to the correlative signal from the quartz microbalance detector, so that the gas stream at the delivery site contains the gas component at the set point concentration.

In a further aspect of the invention relates to a gas component supply system, comprising:

a device for sensing concentration of a gas component in a gas stream, comprising a quartz microbalance detector having a physical adsorbent thereon which reversibly adsorbs the gas component, and which in adsorption and desorption thereof effects a change in the oscillation frequency of the quartz microbalance detector, with means for inputting electrical energy to effect oscillation of the quartz microbalance detector and outputting a signal derived from change in the oscillation frequency of the quartz microbalance detector and correlative of concentration of the gas component in the gas stream;

a gas flow control for regulating the addition of said gas component into said gas stream;

a feedback control circuit operatively connected to said device to receive said signal and arranged to responsively control said gas flow control, to maintain a set point gas concentration level within said gas stream.

In a still further aspect of the invention relates to a system for supplying a gas component in a gas stream to a delivery site at a set point concentration, comprising:

a gas stream flow circuit for flow of the gas stream therethrough to the delivery site;

means for introducing the gas component to the gas stream upstream of the delivery site at adjustably variable rate;

a quartz microbalance detector having a physical adsorbent thereon which reversibly adsorbs the gas component, and which in adsorption and desorption thereof effects a change in the oscillation frequency of the quartz microbalance detector, with means for inputting electrical energy and outputting a detector signal correlative of concentration of the gas component in the gas stream;

means for processing said detector signal, responsively generating a control signal, and adjusting the gas component introducing means via the control signal to introduce the gas component to the gas stream in sufficient quantity and rate to yield the set point concentration of the gas component in the gas stream at the delivery site.

Another aspect of the invention relates to a method of supplying to a delivery site a gas stream containing a gas component at a set point concentration, comprising the steps of:

flowing a source gas stream along a flow path to the delivery site;

adding the gas component to the source gas stream in the flow path upstream of the delivery site to form the gas stream delivered to the delivery site;

providing a quartz microbalance detector having a physical adsorbent thereon which reversibly adsorbs the gas component, and which in adsorption and desorption thereof effects a change in the oscillation frequency of the quartz microbalance detector;

inputting electrical energy to the quartz microbalance detector and outputting a signal correlative of concentration of the gas component in the gas stream;

exposing at least a portion of the gas stream to the quartz microbalance detector to generate the correlative output signal therefrom;

controlling the amount of gas component added to the source gas stream to yield the gas stream flowed to the delivery site, in response to the correlative signal from the quartz microbalance detector, so that the gas stream at the delivery site contains the gas component at the set point concentration.

A still further aspect of the invention relates to a gas supply system for delivering a selected gas component in a multicomponent gas stream to a process unit utilizing same, said system comprising:

(i) a source vessel containing a source of said gas component;

(ii) a carrier gas supply connected to the gas component source vessel by a first gas flow line;

(iii) a mass flow controller in said first gas flow line;

(iv) a discharge line interconnecting the gas component source vessel and the process unit;

(v) a quartz microbalance assembly joined in gas component concentration sensing relationship to the gas discharge line;

(vi) a branch flow line interconnecting the first gas flow line and the gas discharge line;

(vii) a mass flow controller in the branch flow line; and (viii) a signal processing unit joined to the quartz microbalance sensor unit for receiving from the quartz microbalance sensor a signal indicative of concentration of the gas component in the gas stream flow through the gas discharge line, and responsively adjusting one or both of said mass flow controllers, to maintain a selected concentration of gas component in the gas stream flow through the gas discharge line to the process unit.

Other aspects, features and embodiments of the invention will be more fully apparent from the ensuing disclosure and appended claims.

DETAILED DESCRIPTION OF THE INVENTION AND PREFERRED EMBODIMENTS THEREOF

As discussed hereinabove, the variation in film thickness of silicon coatings deriving from trichlorosilane generated from a bubbler source may be as high as 5–10% in conventional practice. The present invention in one embodiment provides a quartz microbalance sensor that responds to the vapor pressure of the tricholorosilane.

While the ensuing description is directed primarily to trichlorosilane systems in which a quartz microbalance is employed to monitor the concentration of such source reagent, it will be appreciated that the utility of the invention is not thus limited, but extends to other gas component species and applications in which it is desired to monitor a component of a process stream, and to deliver such component at a precise, accurate and reproducible concentration level.

The quartz microbalance system of the invention may be utilized in a mode of operation in which the frequency of oscillation of the quartz crystal will depend on the mass of material adsorbed on the surface, in which the frequency of the quartz crystal will be a linear equation of the vapor pressure at constant temperature and pressure conditions, by an equation such as set out below:

$$F = k + x p_v \tag{1}$$

wherein
k=a constant;
x=a coefficient equal to the slope of the frequency change/concentration plot.

Figure 1:
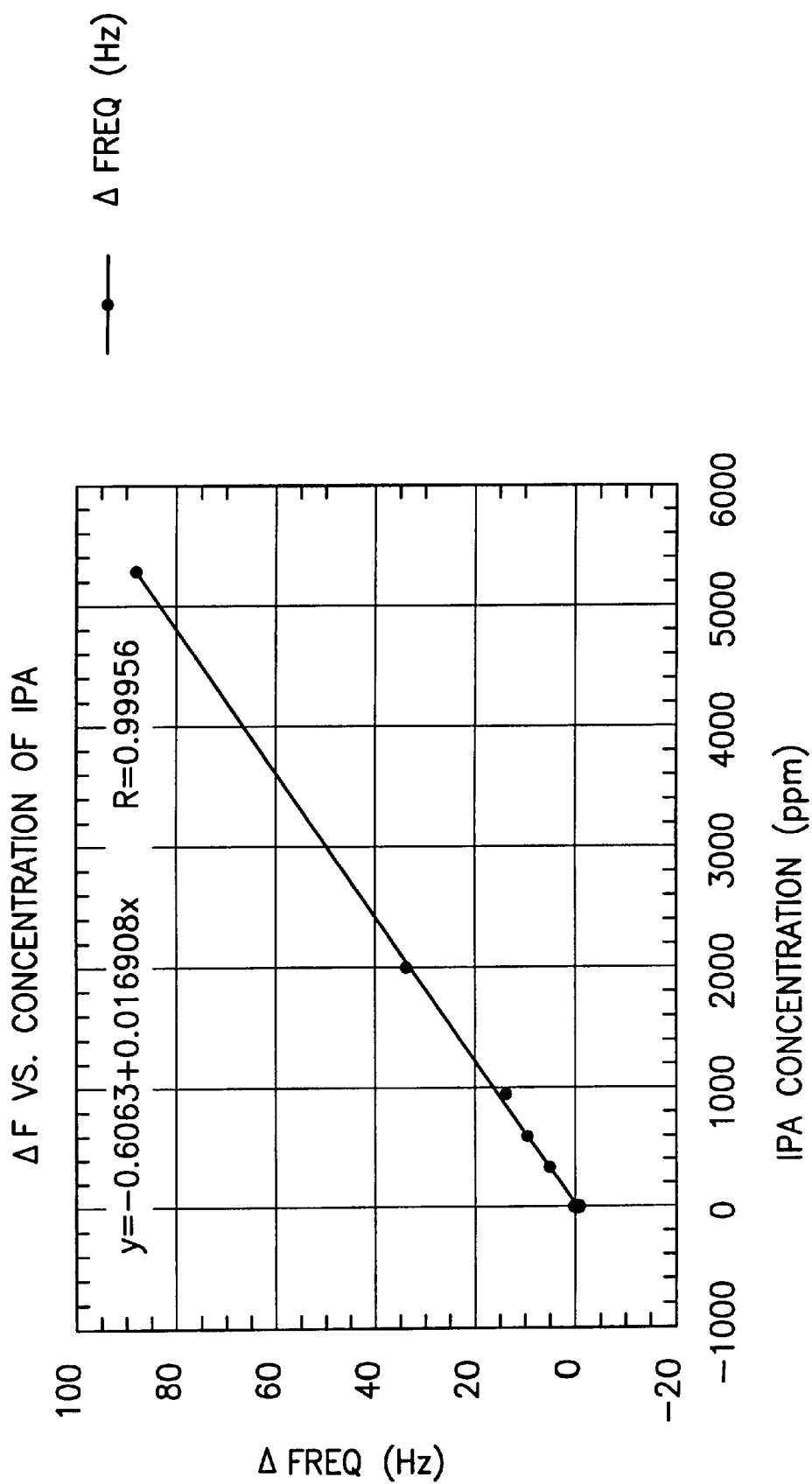
FIG. 1 is a graph of change in frequency as a function of concentration of isopropylalcohol (IPA), as monitored by a crystal coated with Carbowax 400 polyethylene glycol to enhance IPA absorption.

As an example of the foregoing, FIG. 1 is a graph of change in frequency as a function of concentration in parts per million of isopropanol (IPA), as detected by a quartz crystal microbalance coated with Carbowax to enhance adsorption of IPA. Various Carbowax polyethylene glycols and methoxypolyethylene glycols may be employed with molecular weights in the range of from about 200 to about 20,000.

The plot of FIG. 1 shows the linear relationship, for which equation (1) above becomes:

$$F = -0.6063 + 0.016908 p_v \tag{2}$$

The quartz microbalance sensor thereby yields a frequency change that can be related to the concentration, and the change in frequency may be utilized as an output signal from the quartz microbalance detector to regulate the concentration of a selected species in a stream, such as a bubbler outlet stream.

Figure 2:
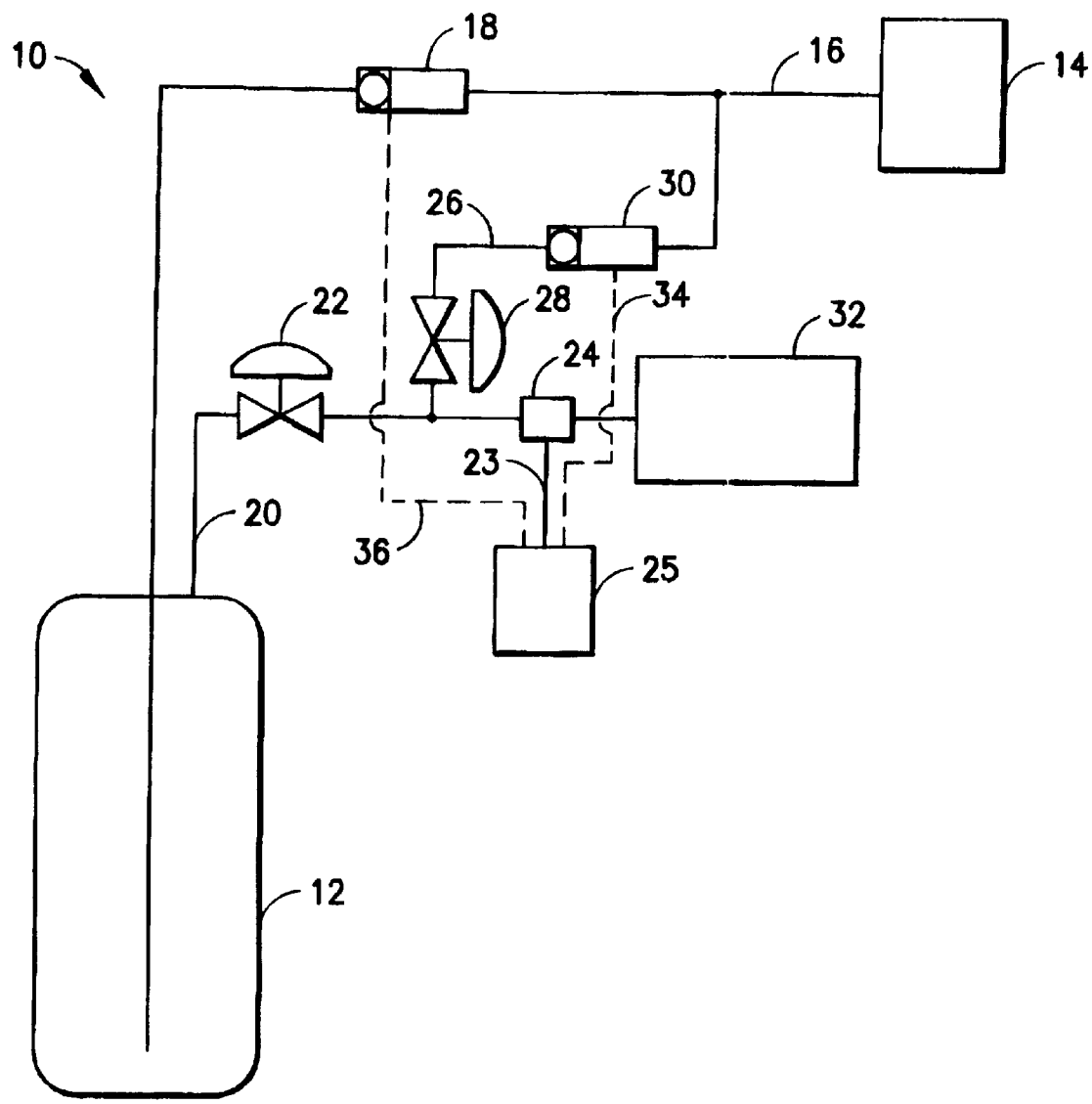
FIG. 2 is a schematic representation of a bubbler control system utilizing a quartz microbalance device in accordance with one embodiment of the present invention.

One such arrangement for regulating concentration of a component in a gas stream is shown in FIG. 2.

As illustrated in FIG. 2, the process system comprises a gas supply apparatus 10 including a bubbler vessel 12 containing a reagent source material (not shown) that is volatized into the carrier gas and transported as hereinafter more fully described to the semiconductor manufacturing facility 32, for use therein.

The bubbler vessel 12 is joined in flow communication, via carrier gas feed line 16 containing mass flow controller 18 therein, with a carrier gas source 14.

Joined to the bubbler vessel 12 is a gas discharge line 20 containing flow control valve 22 and quartz microbalance sensor assembly 24 therein. The gas discharge line 20 conveys gas to the semiconductor manufacturing facility 32. Interposed between carrier gas feed line 16 and gas discharge line 20 is a branch flow line 26 containing flow control valve 28 and mass flow controller 30 therein.

In operation of the FIG. 2 system, carrier gas from carrier source 14, such as a conventional gas cylinder containing carrier gas such as hydrogen, is flowed in line 16 at a flow rate determined by mass flow controller 18 in such line, and mass flow controller 30 in branch line 26. The flow of carrier gas in line 16 enters the bubbler and entrains the source reagent vapor, such as arsine, phosphine or other hydride gas, or an acid gas such as boron trifluoride, hydrogen chloride, boron trichloride, or a halogenated silane or disilane. The resulting multicomponent gas stream containing the volatilized source reagent in the carrier gas then is discharged from bubbler 12 in line 20 and flowed (with flow control valve 22 being open) to the semiconductor manufacturing process 32. The quartz microbalance sensor assembly 24 may be disposed in the main flow line 20 or it may be arranged to monitor a slip-stream constituting a minor portion of the overall flow from line 20. The quartz microbalance sensor assembly 24 includes a quartz crystal with an affinity coating thereon having selective sorptive relationship to the gas component to be monitored.

The quartz microbalance thus experiences a change in its frequency response characteristics as the concentration of the selected component in the gas stream changes. In response to such changes, the quartz microbalance produces a correlative output signal which can be periodically or continuously sampled by an associated electronics module 25 linked to the quartz microbalance assembly 24 by signal transmission cable 23, to produce an output and control signals for modulating the gas supply system, to thereby produce the desired concentration of the monitored component in the gas flowing to the semiconductor manufacturing unit 32.

More specifically, the quartz microbalance assembly 24 may be coupled via the electronics module 25 (including digital programmable computer, microprocessor or other signal processing apparatus or components) in control relationship with the mass flow controller 30 in branch line 26, as schematically represented by the dashed line 34 between sensor assembly 24 and mass flow controller 30, and such sensor assembly 24 may also be coupled in control relationship with mass flow controller 18 in line 16, as schematically represented by dashed line 36. The electronics module 25 also electrically energizes the quartz crystal in the quartz microbalance assembly, in addition to monitoring the crystal's frequency response.

In operation, when the quartz microbalance sensor assembly 24 senses an increase in concentration of the component supplied from bubbler 12, a control signal may be generated by electronics module 25 and passed in signal line 34 to mass flow controller 30, to reduce the flow of carrier gas from line 16 to line 20 through branch line 26, to sufficient extent to re-establish the concentration of the monitored component in the gas flowed to process 32, at a desired concentration level.

Alternatively, or concurrently, the sensor assembly 24 can transmit a control signal via electronics module 25 in signal line 36 to mass flow controller 18 to reduce the flow rate of gas from the bubbler 12, to thereby vary the relative portions of monitored component and carrier gas component in the stream flowed to the process 32.

Conversely, if the sensor assembly 24 senses a decrease in the concentration of the monitored component, electronics module 25 can send a signal in signal line 34 to mass flow controller 30 to reduce the flow rate of carrier gas in branch line 26 to the discharge line 20, and at the same time transmit a signal in signal line 36 to mass flow controller 18, to increase the flux and concentration of the monitored gas component in the gas flowed to process 32.

Thus, the quartz microbalance sensor assembly 24 and electronics module 25 are constructed and arranged to effect modulation of the concentration of the monitored component in the multicomponent gas stream, to maintain a predetermined or set point concentration of the monitored component in the gas flowed to the downstream process unit.

As an illustrative example, the system shown in FIG. 2 could be arranged so that if the concentration in the bubbler above the liquid layer therein were 500 Torr, the control system could be arranged for delivery of the monitored component at a somewhat lower value, such as 490 Torr. The control system in such circumstance would measure the concentration and lower the flow to mass flow controller 18 and increase the flow to mass flow controller 30 to maintain the total flow and concentration at the control set point value.

In this manner, the quartz microbalance control system functions as a flow diverter or mixing valve to modulate the portion of the carrier gas that is flowed through the bubbler or else diverted directly to the discharge line for passage to the downstream complex in which the gas is utilized.

The mass flow controllers have a rapid response time. Alternative modes of flow control, such as changing the temperature of the bubbler, have significantly longer time constants. The mass flow controllers in the FIG. 2 arrangement see only the hydrogen carrier gas and therefore are readily controllable, relative to other possible arrangements in which mass flow controllers may be used for flow control of multicomponent gas streams.

The system shown in FIG. 2 is also readily retrofitted to bubbler systems utilizing a mass flow controller 18 in an existing operation. In such instance, the flow control valves 22 and 28, sensor assembly 24, mass flow controller 30 and branch line 26 would be installed in the existing operation, to retrofit such system for operation in accordance with the present invention.

The electronics module 25 may as mentioned comprise a microprocessor or other signal processing control means, such as an associated computer, clock/cycle timer means, etc. Further, the signals transmitted in signal lines 34 and 36 may be electrical, pneumatic, optical or other type of signal, as appropriate to the specific application and system in which the sensing apparatus and method of the invention are employed.

The quartz microbalance sensor in sensing assembly 24 may utilize an affinity coating which has appropriate affinity characteristics in relation to the gas component to be monitored, and such coating will be selected to be stable in the fluid stream with which same is deployed.

In some instances where trichlorosilane or other halosilane is utilized as the monitored gas component, it may not be necessary to provide any coating on the quartz microbalance crystal surface, since the quartz will have some native concentration of hydroxyl functionality which may permit reversible trichlorosilane interaction with the substrate to form tricholorsiloxy pendant functional groups on the quartz surface. Preferably, however, a porous sol gel coating of silica or other affinity coating will be used, providing sorptive affinity for the halosilane or other component being monitored.

In the gas supply system of the type shown in FIG. 2, other source means than bubblers could be employed, as for example a sorbent-based gas storage and dispensing apparatus of the type shown and described in U.S. Pat. No. 5,518,528 issued May 21, 1996 to Glenn M. Tom and James V. McManus for "Storage and Delivery System for Gaseous Hydride, Halide, and Organometallic Group V Compounds," the disclosure of which hereby is incorporated by reference in its entirety.

The system of the invention may therefore be used in process applications such as silicon epitaxy, wherein dopants such as arsenic, phosphorous and boron are added to the films being grown. In such applications, a very small quantity of high pressure dopant source material could be utilized, e.g., in a dilution manifold, to produce proper doping, with a quartz crystal concentration monitor providing feedback to maintain the proper dopant concentration. In such manner, a concentration monitor with feedback to a mass flow controller on the dopant source gas supply line may be utilized, to produce highly stable dopant stream with a very small inventory of high pressure gas.

For example, a quartz microbalance monitoring system may be utilized in a dopant supply arrangement such as that disclosed in U.S. Pat. No. 4,936,877 issued Jun. 26, 1990 to Steven J. Hultquist and Glenn M. Tom for "Dopant Delivery System for Semiconductor Manufacture," the disclosure of which hereby is incorporated by reference in its entirety.

The present invention thus provides a device for sensing concentration of a gas component in a gas stream, by a quartz microbalance detector that may have a physical adsorbent thereon which reversibly adsorbs the gas component, and which in adsorption and desorption of the gas component effects a change in oscillation frequency of the quartz microbalance detector, as coupled with means for inputting electrical energy and outputting a signal correlative of concentration of the gas component in the gas stream.

Such quartz microbalance detector system of the invention provides for feedback control of gas concentration, with high resolution and high precision resulting in high accuracy.

The measurement from the quartz microbalance is utilized to regulate the delivery of a gas stream component by control of a process variable, such as flow rate, temperature, vapor pressure, etc. of the gas stream component being monitored.

The quartz crystal microbalance system may be arranged to utilize the ΔF, change in frequency, or alternatively the rate of change of frequency, to control the temperature, vapor pressure, flow rate, etc., of the gas component and regulate its concentration.

The quartz crystal microbalance may have coated thereon a physical adsorbent such as alumina, silica, aluminosilicate, carbon, polymeric adsorbent material, or combinations of the foregoing, as well as any other suitable materials having affinity for the gas component of interest, and which are depositable on the quartz microbalance to provide a suitable affinity coating.

In some instances, as mentioned hereinabove, the quartz crystal may be used in a bare (uncoated) form, utilizing surface functionality such as hydroxyl groups to reversibly sorb the gas component of interest, such as a halosilane compound.

Further, the surface of the quartz crystal may be reacted under gas phase reaction conditions to functionalize the surface, e.g., to impart a population of functional groups such as amines, amides, alkoxy, or other functional groups or deposited species on the substrate.

The gas component being monitored in the multicomponent gas stream may be any suitable species as to which the quartz microbalance in uncoated or coated form has sufficient sorptive affinity.

Examples of illustrative gases, which may be monitored within the broad practice of the invention utilizing suitable affinity coatings, include trichlorosilane, trimethylindium, dimethylaluminumhydroxide, tetrachlorotitanium, tetrakisdiethylamidotitanium, tetrakisdimethylamidotitanium, tetraethylorthosilicate, tungsten hexafluoride, copper hexafluoroacetylacetonate vinyl trimethylsilane, pentakisdiethylamidotantalum, dimethylamidotantalum, fluorinated derivatives of tetraethylorthosilicate, trimethylgallium, triethylindium, dichlorosilane, octamethylcyclotetrasiloxane, titaniumisopropoxide, iron pentacarbonyl, isopropanol and trimethylaluminum.

In the practice of the invention, multiple quartz microbalance detector units may be utilized, each with a respective different affinity coating, to monitor respective different components of a multicomponent gas stream.

The quartz crystal utilized in the practice of the present invention may be of any appropriate type. The crystal is cut in the AT direction. When excited by an oscillating electric field, the crystal attempts to oscillate at a well-defined fundamental frequency that is determined by the mass of the crystal. The frequency relationship is:

$$\Delta F = \text{constant} \times \text{mass} \quad (3)$$

The mass on the surface of the quartz crystal, to a first approximation, adds to the total mass of the system. The crystal is not prone to strongly absorb large amounts of material in its native state and the quartz crystal per se is may be and preferably is substantially inert in the medium of interest.

The specificity of the adsorption of the monitored gas component in the process of the invention is determined by the coating material on the quartz crystal surface. The gas species being monitored may reversibly react with the coating material, or alternatively, the material of interest may dissolve in the coating material with the extent of dissolution depending on Henry's law solubility behavior. An example is the detection of isopropanol (IPA) in a multicomponent gas stream, in which a coating of material such as Carbowax 400 is utilized to dissolve the IPA and increase the mass of the quartz crystal.

As another example, a silica may be used to adsorb trichlorosilane and remain stable in the acidic environment. The silica can be deposited on the crystal of the crystal microbalance from a sol gel. Sol gel can be formed from hydrolysis of tetraethylorthosilicate in a water/methanol solvent mix, with the soluble sol gel being spin-coated onto the crystal surface. The base crystal structure may for example comprise a 5 megahertz (MHz) crystal with gold electrodes, which is spin coated with a loading of about 90 micrograms ($\mu$g) of the sol gel-derived silica, to provide a porous, high surface coating on the quartz surface.

The quartz crystal once coated is stabilized and then assessed to determine the frequency of the crystal with the coating in the absence of any adsorbable gas. The quartz crystal then is exposed to the gas stream and the change in frequency of oscillation is monitored to derive the gas concentration as a result of the changes in crystal/coating mass.

In one aspect of the invention, the surface of the quartz microbalance crystal to be exposed to the gas containing the component of interest is utilized with silanol functionality (—OH) on the surface, either native —Si—OH functional groups of the surface, or added —OH groups via a suitable coating, such as by treatment of the surface with a silane or a silazane, to provide a suitable population of —Si—OH functional groups on the surface.

The thinner the coating, the faster the response that is achieved by the quartz microbalance system, when affinity coatings are employed. In general, the thickness should be at least 0.1 micrometer up to about 100 micrometers thickness, however any suitable thickness may be utilized consistent with the specific affinity coating and gas species being monitored.

The hydroxy-functional surface in the above-described illustrative system of the invention may be used to monitor a halogen- and/or alkyl-containing gas species of interest, such as by the following surface reactions:

quartz surface-Si—OH+QX→quartz surface-Si—O—Q+HX  (4)

for a gas component QX, where X is halogen (Cl, Br, I, or F) functionality covalently bonded to the gas moiety Q, or quartz surface-Si—OH+AR→quartz surface-Si—O—R+AH  (5)

for a gas component AR, where R is a $C_1$–$C_8$ alkyl functionality covalently bonded to the gas moiety A.

As a specific example of reaction (4), for trichlorosilane as the gas component to be monitored, quartz surface-Si—OH+SiCl$_4$→quartz surface-Si—
O—SiCl$_3$+HCl  (4a)

and as a specific example of reaction (5), for allane as the gas component to be monitored, quartz surface-Si—OH+AlH$_3$→quartz surface-Si—
O—AlH$_2$+H$_2$  (5a)

Thus, the quartz microbalance surface, functionalized with —Si—OH functionality, is exposed to the gas stream of interest containing a component to be monitored, having —X (halo) or —R (alkyl) functionality. Upon contacting of the halo- or alkyl-functional gas species of interest, the —Si—OH functionality of the quartz microbalance surface reacts with the halogen or alkyl functionality of the gas species, to yield a reversibly bound reaction product on the crystal surface whose presence changes the frequency response of the crystal and permits the frequency change to produce a signal correlative of the gas concentration, as previously described.

Subsequent to the use of the quartz microbalance, the surface bearing the bound reaction product may be regenerated simply by exposure to ambient air with relative humidity, to repopulate the quartz crystal surface with —OH functionality, by reaction of the bound reaction product functionality with atmospheric moisture. After such repopulation of the surface with —OH functionality, the quartz microbalance crystal can again be placed in service.

Such regeneration of the quartz crystal may thus be carried out in situ, between periods of operational monitoring, to simply and readily reconstitute the surface, for renewed active monitoring of the gas stream of interest.

Figure 3:
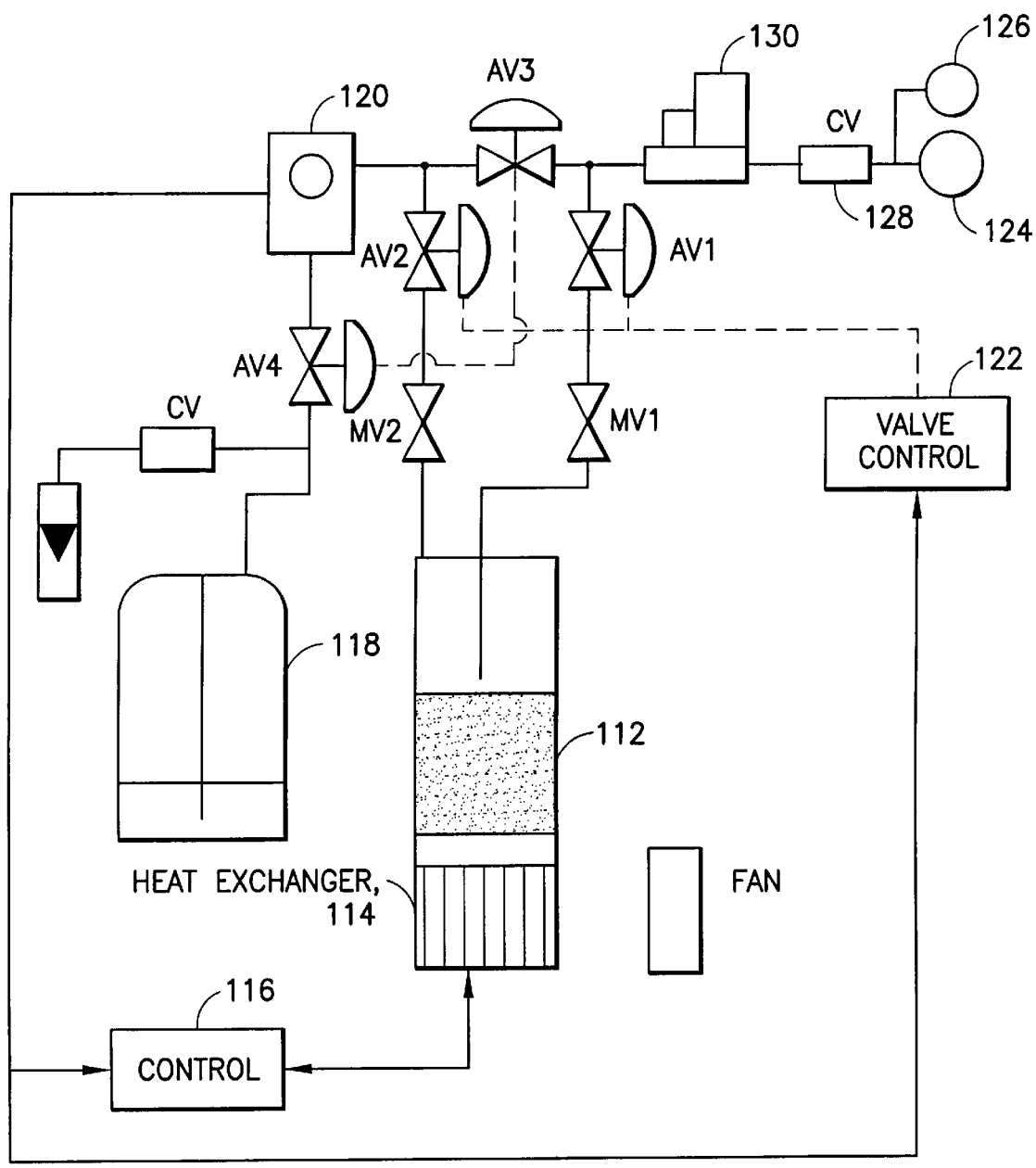
FIG. 3 is a schematic representation of a system for detecting, monitoring and regulating gas concentration in accordance with an embodiment of the present invention.

Referring again to the drawings, FIG. 3 is a schematic representation of a control system for monitoring and regulation of constituent gases, according to another embodiment of the invention.

The system illustrated in FIG. 3 includes a bubbler 112 containing trichlorosilane (TCS), a heat exchanger 114 for the bubbler 112 and a control 116 for the heat exchanger 114. The gas from the bubbler 112 flows through MV1, MV2, AV1, AV2, and AV3, through valve AV4 and into the chamber 118. Quartz microbalance 120 is exposed to the gas flow stream to monitor gas concentration. The detected ΔF of the microbalance is sent to the heat exchanger control 116 and to the valve control 122 to regulate gas concentration and flow. The system under control typically can also include an inert gas source 124 providing an inert gas such as nitrogen, with a regulator 126 and associated metering controls including check valve 128 and mass flow controller 130.

In such system, the temperature of the bubbler and the quartz microbalance chamber are independently controllable.

The system shown in FIG. 3 in operation is capable of 9-bit resolution of trichlorosilane vapor pressure measurements, and requires about 5 seconds to achieve the 9-bit resolution.

Figure 4:
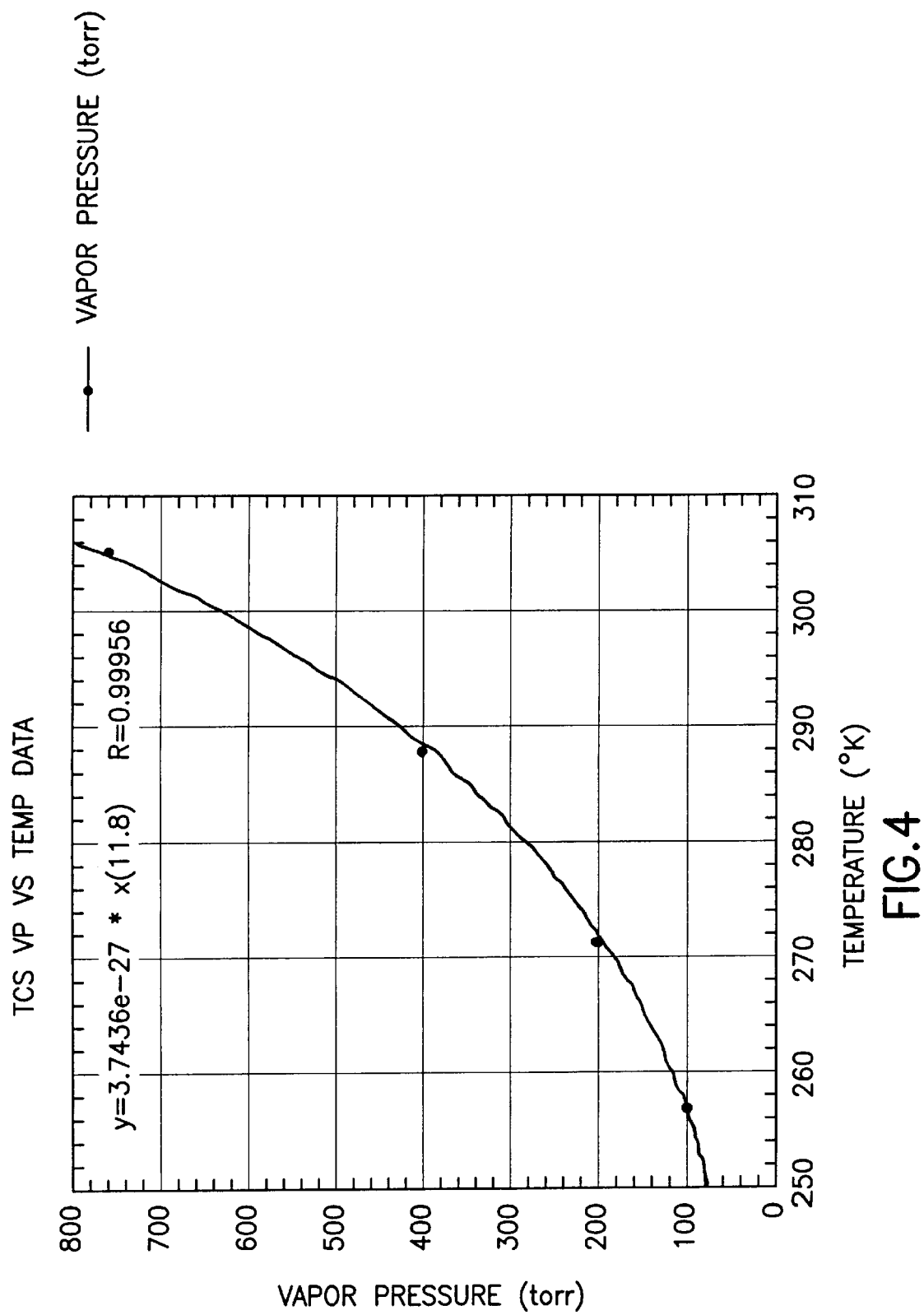
FIG. 4 is a graph of vapor pressure of trichlorosilane as a function of temperature in a trichlorosilane bubbler.

FIG. 4 is a plot of vapor pressure as a function of temperature for trichlorosilane.

Examination of this vapor pressure curve shows that change in vapor pressure will be on the order of 3.4%/° C. at 25° C. It is likely that the bulk of variability of thickness of silicon deposited from trichlorosilane in conventional practice is due to change in the temperature in the liquid evaporating in the bubbler. The vapor pressure therefore is a strong function of temperature in the bubbler. This functional relationship shows that monitoring of concentration and corresponding modulation of the temperature is one approach for achieving control of the concentration of trichlorosilane delivered by a bubbler assembly in a silicon deposition operation.

The features and advantages of the present invention are more fully illustrated by the following non-limiting examples.

EXAMPLE 1

In this experiment, a bubbler was filled with acetone, and the resulting vapor was contacted with a quartz microbalance sensor. The frequency and bubbler temperature were determined as a function of time for this system.

The quartz microbalance sensor used for monitoring concentration of the acetone was a 5 megahertz crystal with gold electrodes (ICM, Oklahoma City, Okla.), on which was deposited a silica coating from a sol gel. The sol gel was formed by hydrolysis of tetraethylorthosilicate (TEOS) in a water/methanol solvent mix. The sol gel was spin coated onto the quartz crystal, at a loading of 90 micrograms ($\mu$g).

Figure 5:
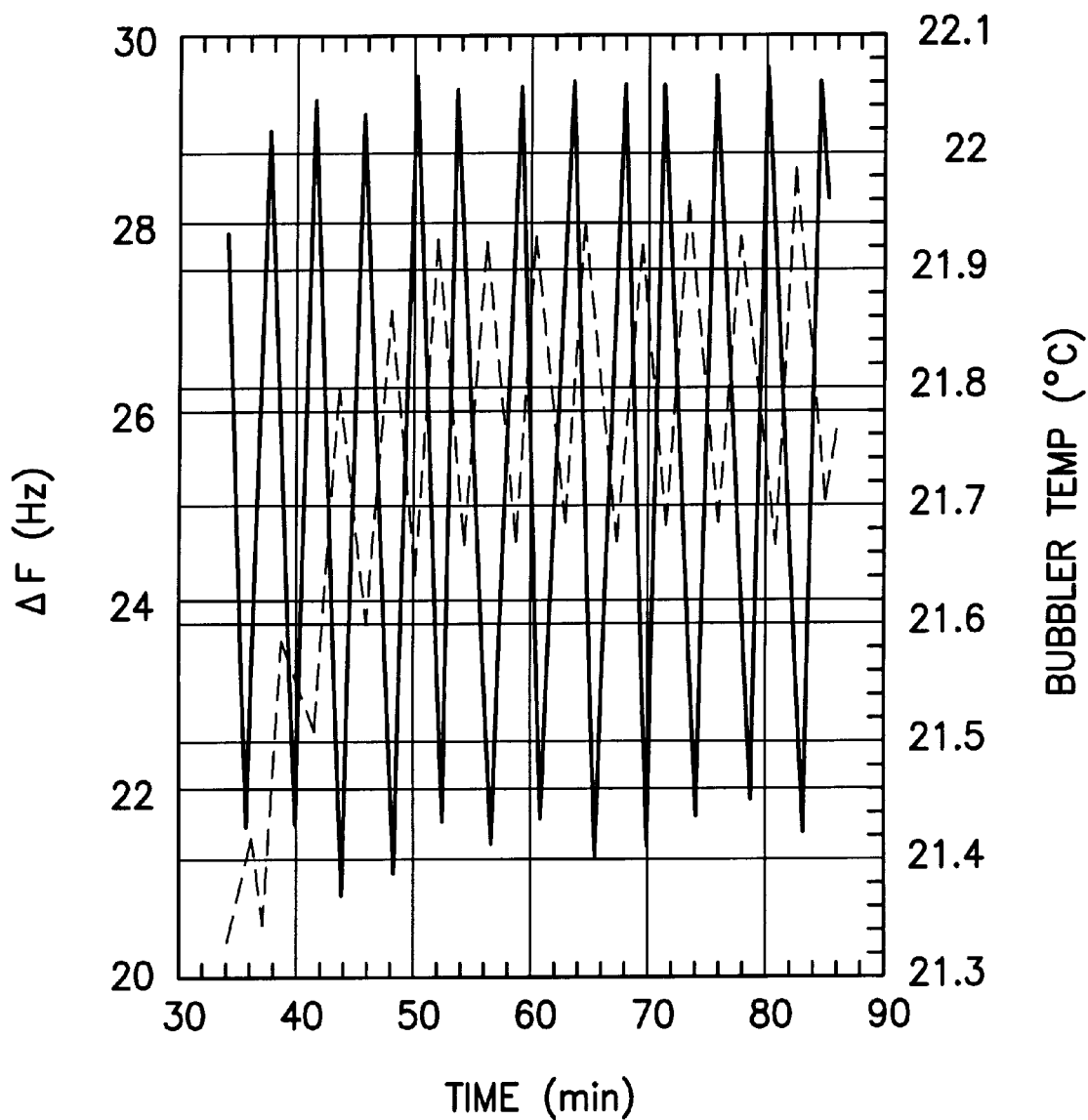
FIG. 5 is a graph illustrating the relationship between the temperature of an acetone bubbler and the frequency of a quartz microbalance, as a function of time.

The plot of FIG. 5 shows that the frequency and temperature are 90° out of phase. The reason for this phase shift is that as the temperature decreases, less acetone is present in the gas stream. A lower acetone concentration therefore results in a decreased amount of acetone on the quartz microbalance, which in turn causes the frequency to increase.

EXAMPLE 2

In this example, a 5 megahertz crystal with gold electrodes (ICM, Oklahoma City, Okla.) was coated with a silica coating from a sol gel. The sol gel was formed by hydrolysis of tetraethylorthosilicate (TEOS) in a water/methanol solvent mix. The soluble sol gel was spin coated on the quartz crystal, at a loading of 90 micrograms ($\mu$g).

The bubbler was filled with trichlorosilane (99% purity, Aldridge Chemical Company).

Figure 6:
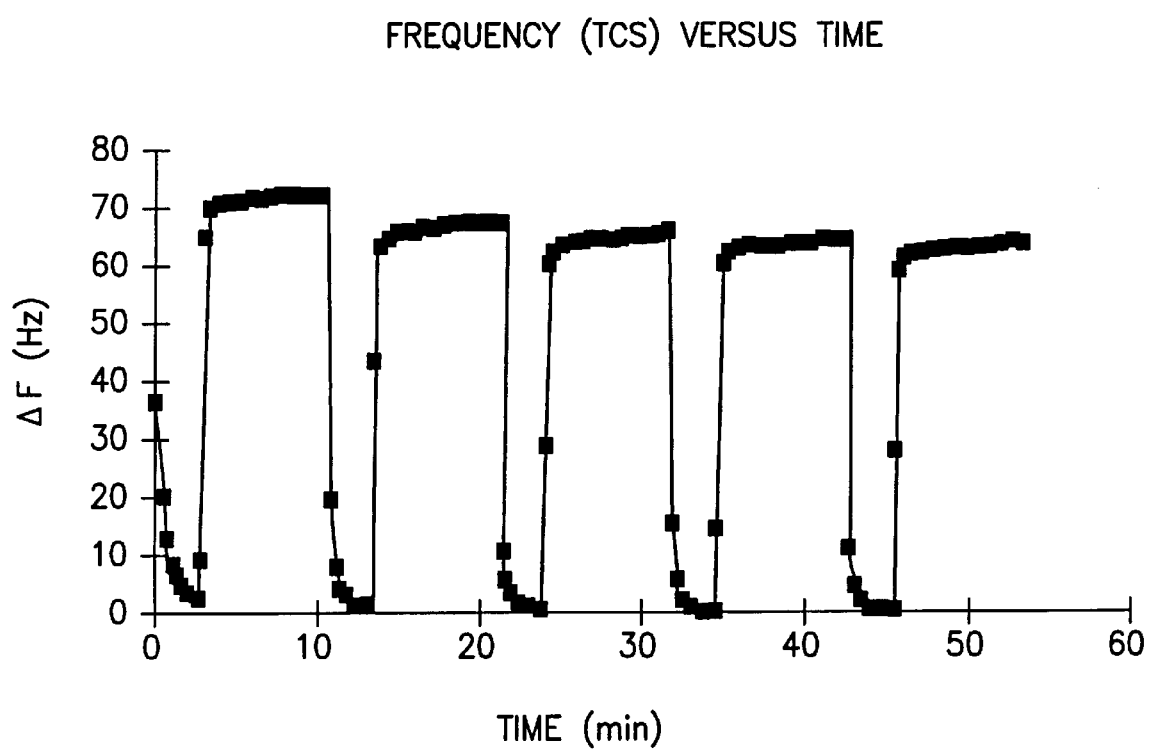
FIG. 6 is a graph of the frequency of the quartz microbalance in a trichlorosilane bubbler system as a function of time.

FIG. 6 shows the change in frequency as a function of time. The temperature of the bubbler was allowed to oscillate while flowing a mixture of nitrogen and trichlorosilane across the sensor surface at 40° C.

Figure 7:
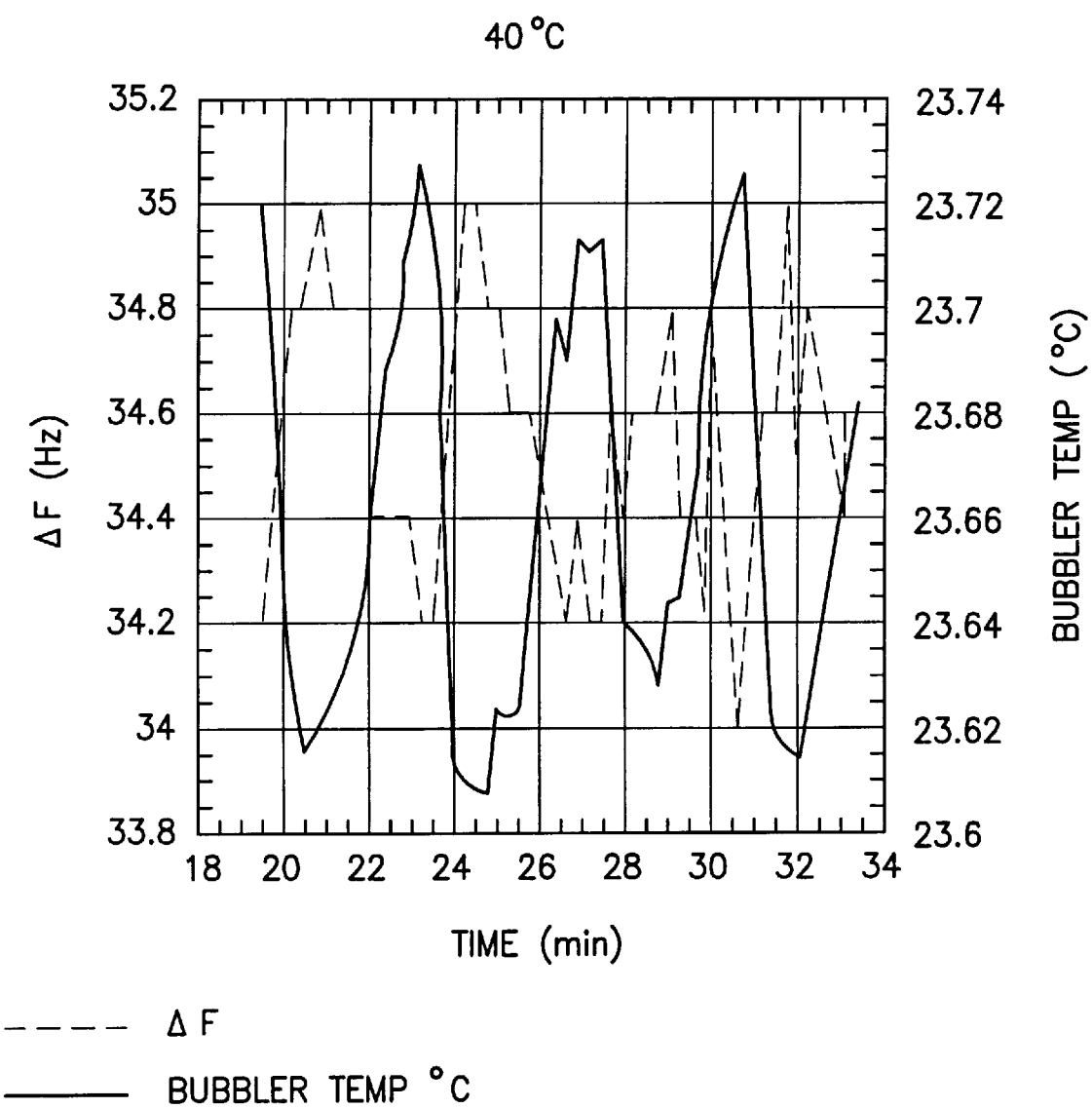
FIG. 7 is a graph of frequency change and trichlorosilane bubbler temperature as a function of time, for trichlorosilane detected by a TEOS-coated quartz crystal microbalance.

FIG. 7 is a plot of frequency and bubbler temperature as a function of time for the system.

It can be seen that the response of the quartz microbalance detector was crisp. There appear to be no very fast processes that caused drift in the frequency with time. The changes in the high frequency portion of the curve (no TCS) show a drift that is stabilizing.

The ΔF for acetone under similar conditions was about 350 hertz, while the ΔF value was about 70 hertz for trichlorosilane. The lower sensitivity indicates that the trichlorosilane does not bind as strongly as acetone on the silica.

The resolution obtained using a 5 second gate was 0.2 Hertz. Such resolution in conjunction with the ΔF value of 70 hertz yields almost 9-bit resolution. These data indicate that the desired precision was achieved.

Next, the temperature of the quartz microbalance chamber was lowered from 40° C. to 30° C. The change in the set-point occurred at 40 minutes after inception of operation. The shift in the signal frequency was doubled.

Figure 8:
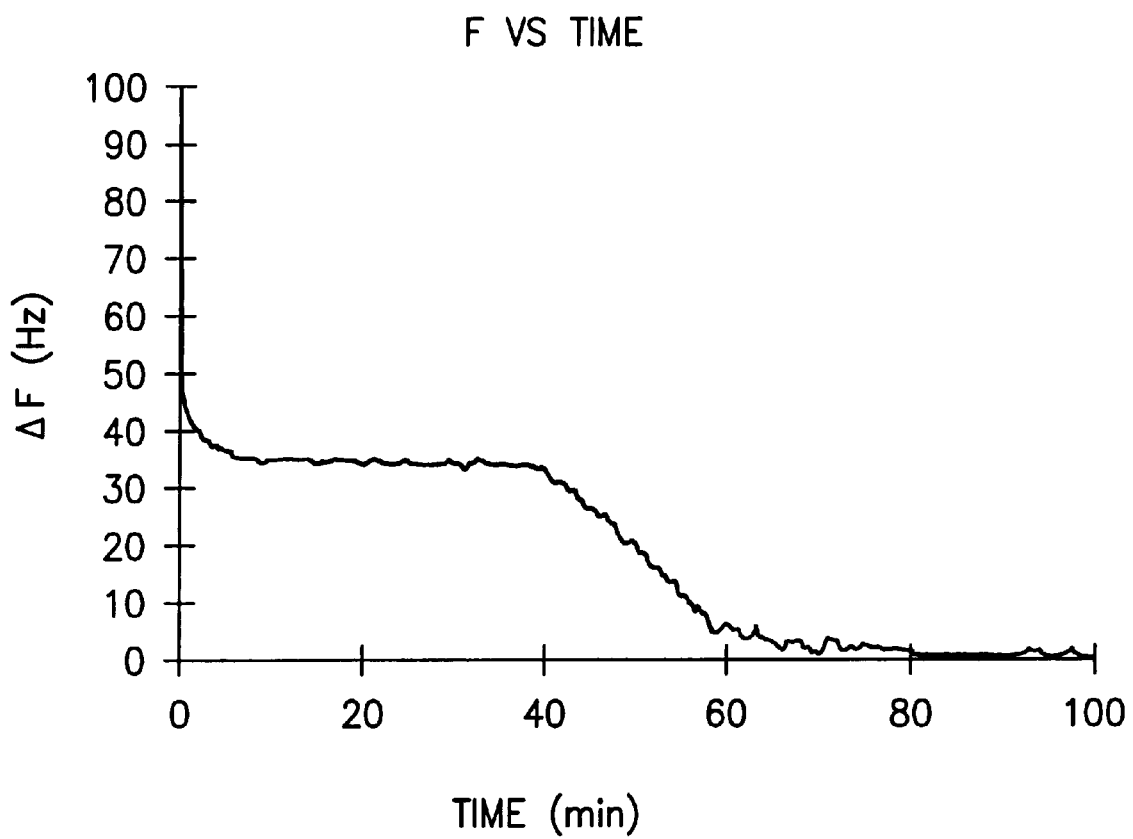
FIG. 8 is a function of frequency change as a function of time, for trichlorosilane monitored by a TEOS-coated quartz crystal microbalance.
Figure 9:
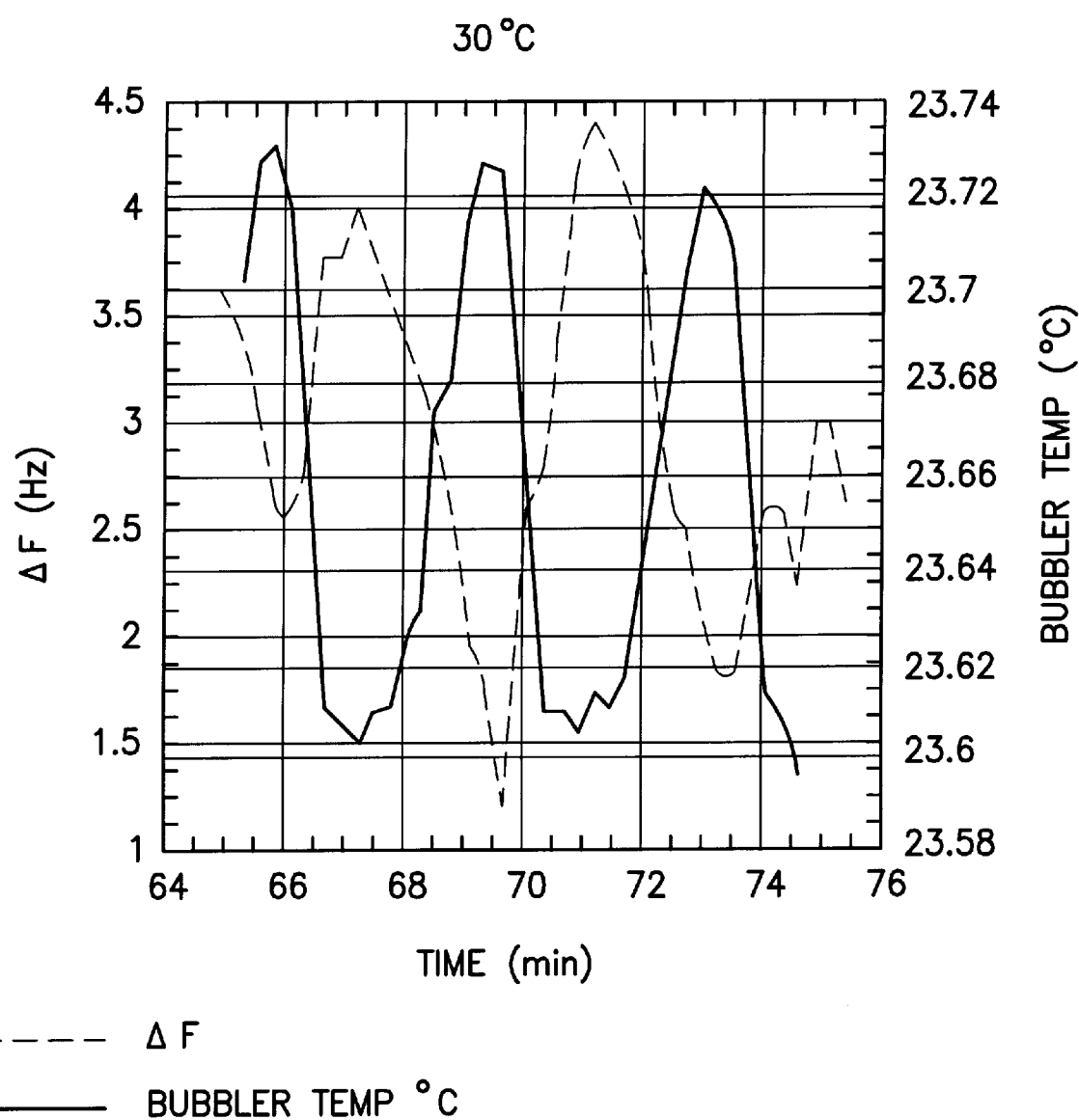
FIG. 9 is a graph of frequency change and bubbler temperature as a function of time for a quartz crystal microbalance monitoring trichlorosilane at 30° C.

FIG. 8 is a plot of frequency as a function of time, and FIG. 9 is a plot of change in frequency and bubbler temperature as a function of time for trichlorosilane at 30° C. for the quartz microbalance chamber. The lower temperature permits higher adsorption of the trichlorosilane on the quartz microbalance and the sensitivity is increased. The sensitivity factor when the quartz microbalance is at 40° is 12.5 hertz/° C. The value doubles when the quartz microbalance temperature is lowered to 30°, to 25 hertz/° C.

A frequency response function therefore can be defined as:

$$\Delta F = 0.12 \text{ hertz/torr} \times p_v$$

where $p_v$ is the vapor pressure in torr.

Since temperature changes of several degrees in the bubbler are expected in normal operation of the system, the resolution evidenced by the sensor is adequate to provide a superior level of process control when combined with an appropriate process control system.

When the temperature change in the bubbler was increased, the change in the frequency was correspondingly increased.

Figure 10:
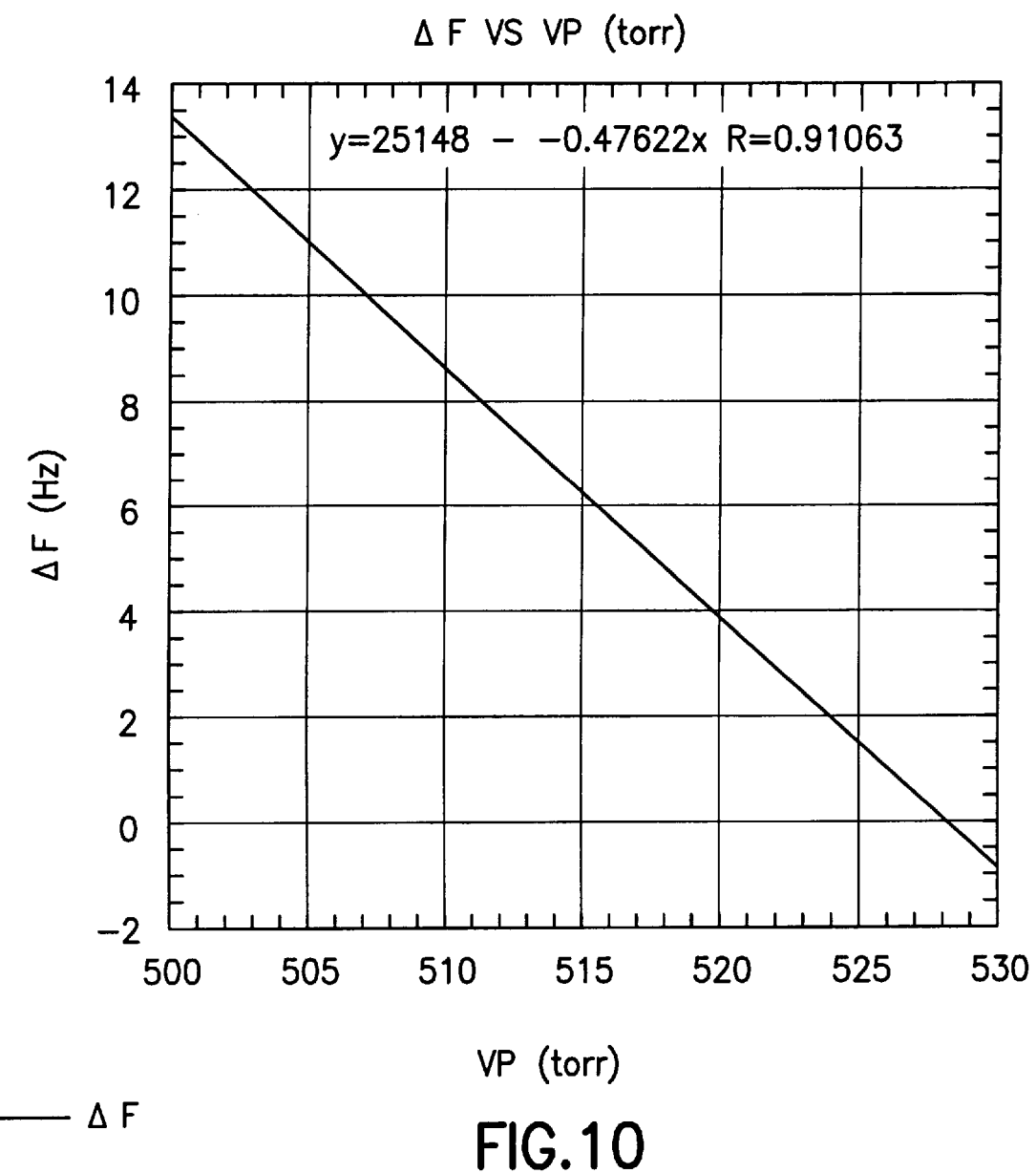
FIG. 10 is a function of frequency change as a function of vapor pressure for trichlorosilane delivered from a bubbler.

A plot of ΔF as a function of vapor pressure in torr is set out in FIG. 10. The sensitivity of the quartz microbalance in this application is −0.4622 Hertz/Torr in the vicinity of 500 Torr.

Response time in this quartz microbalance sensor was controlled by the following factors:

Flow rate across the sensor. The faster the flow rate of the gas across the sensor face, the quicker the sensor will respond. The rate of equilibration under laminar flow conditions is proportional to the flow rate of the gas to the ½ power. Under turbulent conditions, the response can be as high as flow rate to the ¾ power. Control of the flow rate parameter may be achieved through appropriate design. A flow-through cell containing the quartz microbalance will have a high rate of response, and dead-ended designs wherein the quartz microbalance is in a closed flow path will have slower response.

Film thickness. The thickness of the coating is inversely related to the square of the response time. With a 90 microgram loading of the affinity coating (silica), the response time is in the range of 15 seconds. A higher loading would yield a greater sensitivity but slower response time. The optimum of loading and associated sensitivity and response time for a given affinity coating and gas stream composition may be readily determined within the skill of the art without undue experimentation.

Electronic design effects. The measurement of frequency is accomplished by counting the number of cycles that occur in a space of time called a gate. If the gate is one second long, then the system can resolve one Hertz. If the gate is 10 seconds, then the system can resolve 0.1 Hertz. If 0.1 hertz resolution is required, then once every 10 seconds is as fast as this system will produce a change in a reading.

The foregoing results show that the quartz microbalance sensor system of the invention is capable of achieving a high level of resolution and effective responsivity for monitoring the concentration of a gas component in a multicomponent gas stream.

The quartz microbalance sensor of the invention may be usefully employed for delivery of a selected component of a multicomponent stream at a desired (set point) concentration, by combining the sensor with appropriate feedback and control means, to regulate the addition of the component to the gas stream at its point of mixing formation. Alternatively, the rate of addition of a carrier gas to a selected component may be modulated to achieve the desired concentration characteristics of the final mixed gas stream.

Accordingly, while the invention has been described illustratively herein with reference to specific embodiments, features and modifications, it will be appreciated that the utility of the invention is not thus limited, but rather extends to other modifications, features and embodiments, and accordingly the invention is to be broadly construed as including within its scope all such variation, modifications and other embodiments.

What is claimed is:

1. A system for sensing concentration of a gas component in a gas stream, wherein the gas component is reversibly reactive with hydroxyl functionality, said system comprising:

(a) a device for sensing concentration of a gas component in a gas stream, said device comprising:
      (i) a quartz crystal microbalance including a quartz crystal with a surface functionalized with hydroxyl functionality which reversibly reacts with the gas component to yield a surface-bound reaction product that (1) effects a change in the oscillation frequency of the quartz crystal and (2) subsequent to reaction is regenerable in the presence of water vapor to re-establish the hydroxyl functionality on said surface; and
      (ii) means for sensing the oscillation frequency of the quartz crystal and generating an output correlative of the concentration of the gas component in the gas stream
   (b) a source of water vapor arranged in fluid communication with the quartz crystal microbalance for re-establishing the hydroxyl functionality on the surface of the quartz crystal microbalance.

2. The system according to claim 1, wherein the surface of the quartz crystal is utilized with only native silanol hydroxy functionality on the surface.

3. The system according to claim 1, wherein the surface of the quartz crystal has been coated with a hydroxyl-functional material to provide a population of —OH functional groups on the surface.

4. The system according to claim 1, wherein the hydroxyl functionality is provided by a coating on the surface of the quartz crystal, of a material selected from the group consisting of polyvinylalcohol (PVA), dextrans, and polystyrene divinylbenzene.

5. The system according to claim 1, wherein the means for sensing the oscillation frequency of the quartz crystal and generating an output correlative of the concentration of the gas component in the gas stream comprise a computational module constructed and arranged to determine the concentration of the gas component in the gas stream by change in the oscillation frequency of the quartz crystal upon reversible reaction of the gas component with the hydroxyl functionality on the surface of the quartz crystal microbalance.

6. The system according to claim 5, wherein the computational module comprises a programmable digital computer.

7. The system according to claim 5, wherein the computational module comprises a microprocessor.

8. The system according to claim 5, wherein the computational module is arranged to determine the concentration of the gas component in the gas stream based on the rate of change of the oscillation frequency of the quartz crystal.

9. The system according to claim 1, wherein the hydroxyl functionality is provided by a coating on the surface of the quartz crystal, of a material selected from the group consisting of hydroxy-functional organic coatings, and carbonaceous waxes having hydroxyl functionality.

10. A method of determining the concentration of a gas component in a gas mixture comprising same, wherein the gas component is reversibly reactive with hydroxyl functionality, and said hydroxyl functionality is regenerable in the presence of water vapor to re-establish the hydroxyl functionality, the method comprising the steps of:

(a) providing a quartz crystal microbalance including a quartz crystal with a surface functionalized with hydroxyl functionality which reversibly reacts with the gas component to yield a surface-bound reaction product that (1) effects a change in the oscillation frequency of the quartz crystal and (2) subsequent to reaction is regenerable in the presence of water vapor to re-establish the hydroxyl functionality on said surface;

(b) sensing the oscillation frequency of the quartz crystal and generating an output correlative of the concentration of the gas component in the gas stream;

(c) subsequent to the sensing of the oscillation frequency, regenerating the functionalized surface in the presence of water vapor to re-establish the hydroxyl functionality on said surface.

11. A method according to claim 10, wherein said gas component is a halide gas species.

12. A method according to claim 10, wherein subsequent to the sensing of the oscillation frequency of the quartz crystal, the surface bearing the bound reaction product is regenerated by exposure to ambient air with relative humidity, to repopulate the quartz crystal surface with —OH functionality, by reaction of the bound reaction product with atmospheric moisture.

13. A method according to claim 12, wherein the regeneration of the quartz crystal is carried out in situ, between periods of generating said output correlative of the concentration of the gas component in the gas stream, to reconstitute the surface for determining the concentration of the gas component in the gas mixture comprising same.

14. A method according to claim 10, wherein said output correlative of the concentration of the gas component in the gas stream is generated based on the change of the oscillation frequency of the quartz crystal upon reversible reaction of the gas component with the hydroxyl functionality on the surface of the quartz crystal.

15. A method according to claim 10, wherein said output correlative of the concentration of the gas component in the gas stream is generated based on the rate of change of the oscillation frequency of the quartz crystal upon reversible reaction of the gas component with the hydroxyl functionality on the surface of the quartz crystal.

16. A method according to claim 10, wherein the gas component in the gas mixture comprising same, is selected from the group consisting of trichlorosilane, trimethylindium, dimethylaluminumhydroxide, tetrachlorotitanium, tetrakisdiethylamidotitanium, tetrakisdimethylamidotitanium, tetraethylorthosilicate, tungsten, hexafluoride, copper hexafluoroacetylacetonate, vinyl trimethylsilane, pentakisdiethylamidotantalum, dimethylamidotantalum, fluorinated derivatives of tetraethylorthosilicate, trimethylgallium, triethylindium, dichlorosilane, octamethylcyclotetrasiloxane, titaniumisopropoxide, iron pentacarbonyl, isopropanol and trimethylaluminum.

17. A method of monitoring partial pressure or vapor pressure of a halo-functional gas in a bubbler, comprising the steps of:

(a) providing a quartz crystal microbalance including a quartz crystal with a surface functionalized with silanol functionality, said silanol functionality having a hydroxyl functionality which reversibly reacts with the halo-functionality of the gas component to yield a surface-bound reaction product which effects a change in the oscillation frequency of the quartz crystal;

(b) sensing the oscillation frequency of the quartz crystal and generating an output correlative of the concentration of the halo-functional gas component in the gas stream;

(c) converting such output to a value of the partial pressure or vapor pressure of the halo-functional gas in the bubbler; and (d) subsequent to the sensing of the oscillation frequency, regenerating the functionalized surface in the presence of water vapor to re-establish the hydroxyl functionality on said surface.

18. A system for supplying a gas component in a gas stream to a delivery site at a set point concentration, comprising:

(a) a gas stream flow circuit for flow of the gas stream therethrough to the delivery site;

(b) means for introducing the gas component to the gas stream upstream of the delivery site at adjustably variable rate;

(c) a quartz microbalance detector including a quartz crystal with a hydroxyl surface functionality that reversibly reacts with the gas component to form a bound reaction product on the surface and effects a change in the oscillation frequency of the quartz microbalance detector, with means for inputting electrical energy to the quartz crystal and outputting a detector signal therefrom that is correlative of concentration of the gas component in the gas stream;

(d) a source of water vapor arranged in fluid communication with the quartz crystal microbalance for re-establishing the hydroxyl functionality on the surface of the quartz crystal microbalance; and (e) means for processing said detector signal, responsively generating a control signal, and adjusting the gas component introducing means via the control signal to introduce the gas component to the gas stream in sufficient quantity and rate to yield the set point concentration of the gas component in the gas stream at the delivery site.

19. A method of supplying to a delivery site a gas stream containing a gas component at a set point concentration, comprising the steps of:

(a) flowing a source gas stream along a flow path to the delivery site;

(b) adding the gas component to the source gas stream in the flow path upstream of the delivery site to form the gas stream delivered to the delivery site;

(c) providing a quartz microbalance detector including a quartz crystal with a hydroxyl surface functionality that reversibly reacts with the gas component to form a reaction product bound to the surface that effects a change in the oscillation frequency of the quartz microbalance detector;

(d) inputting electrical energy to the quartz microbalance detector and outputting a signal therefrom correlative of concentration of the gas component in the gas stream;

(e) exposing at least a portion of the gas stream to the quartz microbalance detector to generate the correlative output signal therefrom;

(f) controlling the amount of gas component that is added to the source gas stream to yield the gas stream flowed to the delivery site, in response to the correlative signal from the quartz microbalance detector, so that the gas stream at the delivery site contains the gas component at the set point concentration;

(g) subsequent to the sensing of the oscillation frequency, regenerating the functionalized surface in the presence of water vapor to re-establish the hydroxyl functionality on said surface.

20. A method according to claim 10, wherein the gas component comprises a halosilane component.

21. A method according to claim 10, wherein the gas component comprises a trichlorosilane component.

22. A method according to claim 10, wherein the gas component comprises a metalalkyl component.

23. A gas component supply system, comprising:
(a) a device for sensing concentration of a gas component in a gas stream, comprising a quartz microbalance detector having a physical adsorbent thereon having a hydroxyl functionality which reversibly adsorbs the gas component, and which in adsorption and desorption thereof effects a change in the oscillation frequency of the quartz microbalance detector, with means for inputting electrical energy to effect oscillation of the quartz microbalance detector and outputting a signal derived from change in the oscillation frequency of the quartz microbalance detector and correlative of concentration of the gas component in the gas stream;
(b) a source of water vapor arranged in fluid communication with the quartz crystal microbalance for reestablishing the hydroxyl functionality on the surface of the quartz crystal microbalance;
(c) a gas flow control for regulating the addition of said gas component into said gas stream; and
(d) a feedback control circuit operatively connected to said device to receive said signal and arranged to responsively control said gas flow control, to maintain a set point gas concentration level within said gas stream.

24. A system according to claim 23, wherein said physical adsorbent is a polymeric adsorbent material selected from the group consisting of polyethers, polyvinylalcohols, and polysiloxanes.

25. A system according to claim 23, further comprising a housing containing said quartz microbalance detector.

26. A system for supplying a gas component in a gas stream to a delivery site at a set point concentration, comprising:
(a) a gas stream flow circuit for flow of the gas stream therethrough to the delivery site;
(b) means for introducing the gas component to the gas stream upstream of the delivery site at adjustably variable rate;
(c) a quartz microbalance detector having a physical adsorbent thereon having a hydroxyl functionality which reversibly adsorbs the gas component, and which in adsorption and desorption thereof effects a change in the oscillation frequency of the quartz microbalance detector, with means for inputting electrical energy and outputting a detector signal correlative of concentration of the gas component in the gas stream;
(d) a source of water vapor arranged in fluid communication with the quartz crystal microbalance for re-establishing the hydroxyl functionality on the surface of the quartz crystal microbalance; and
(e) means for processing said detector signal, responsively generating a control signal, and adjusting the gas component introducing means via the control signal to introduce the gas component to the gas stream in sufficient quantity and rate to yield the set point concentration of the gas component in the gas stream at the delivery site.

27. A system according to claim 26, wherein the means for introducing the gas component to the gas stream upstream of the delivery site at adjustably variable rate include a gas component source vessel, a feed line interconnecting the source vessel and the flow circuit, and an adjustable flow control valve in the feed line.

28. A system according to claim 26, wherein the means for processing said detector signal, responsively generating a control signal, and adjusting the gas component introducing means via the control signal to introduce the gas component to the gas stream in sufficient quantity and rate to yield the set point concentration of the gas component in the gas stream at the delivery site, include a digital computer programmed for said signal processing and generation, and coupled by signal transmission means to the detector and the gas component introducing means.

29. A method of supplying to a delivery site a gas stream containing a gas component at a set point concentration, comprising the steps of:
(a) flowing a source gas stream along a flow path to the delivery site;
(b) adding the gas component to the source gas stream in the flow path upstream of the delivery site to form the gas stream delivered to the delivery site;
(c) providing a quartz microbalance detector having a physical adsorbent thereon having a hydroxyl functionality which reversibly adsorbs the gas component, and which in adsorption and desorption thereof effects a change in the oscillation frequency of the quartz microbalance detector;
(d) inputting electrical energy to the quartz microbalance detector and outputting a signal correlative of concentration of the gas component in the gas stream;
(e) exposing at least a portion of the gas stream to the quartz microbalance detector to generate the correlative output signal therefrom;
(f) controlling the amount of gas component added to the source gas stream to yield the gas stream flowed to the delivery site, in response to the correlative signal from the quartz microbalance detector, so that the gas stream at the delivery site contains the gas component at the set point concentration;
(g) subsequent to the sensing of the oscillation frequency, regenerating the functionalized surface in the presence of water vapor to re-establish the hydroxyl functionality on said surface.

30. A method according to claim 29, wherein the physical adsorbent comprises a material selected from the group consisting of alumina, silica, aluminosilicates, carbon, and polymeric adsorbent materials.

31. A method according to claim 29, wherein said physical adsorbent is a polymeric adsorbent material selected from the group consisting of polyethers, polyvinylalcohols, and polysiloxanes.

32. A gas supply system for delivering a selected gas component in a multicomponent gas stream to a process unit utilizing same, said system comprising:
(a) a source vessel containing a source of said gas component;
(b) a carrier gas supply connected to the gas component source vessel by a first gas flow line;
(c) a mass flow controller in said first gas flow line;
(d) a discharge line interconnecting the gas component source vessel and the process unit;
(e) a quartz microbalance assembly joined in gas component concentration sensing relationship to the gas discharge line;
(f) a branch flow line interconnecting the first gas flow line and the gas discharge line;
(g) a mass flow controller in the branch flow line; and
(h) a signal processing unit joined to the quartz microbalance assembly for receiving an output from the quartz microbalance assembly indicative of the concentration of the gas component in the gas stream flow through the gas discharge line, and responsively adjusting one or both of said mass flow controllers, to maintain a selected concentration of gas component in the gas stream flow through the gas discharge line to the process unit.

33. A system according to claim 32, wherein the gas component source vessel comprises a bubbler.

34. A system according to claim 32, wherein the gas component source vessel comprises a sorbent-based gas storage and dispensing vessel.

35. A system according to claim 32, wherein the process unit comprises a semiconductor manufacturing facility.

36. A system according to claim 32, further comprising a valve in the gas discharge line, upstream of the branch flow line connection with the gas discharge line, and upstream of the quartz microbalance sensor.

37. A system according to claim 36, further comprising a flow control valve in the branch flow line.

38. A system according to claim 32, wherein the signal processing unit comprises a programmable digital computer programmed for maintaining the selected concentration of gas component in the gas stream flowed through the gas discharge line to the process unit.

39. A system according to claim 32, wherein the quartz microbalance assembly comprises a piezoelectric crystal coated with a material having reversible sorptive affinity for the gas component.

40. A system according to claim 39, wherein said material comprises hydroxyl functionality.

41. A system according to claim 32, wherein the gas component source vessel comprises a bubbler containing trichlorosilane.

42. A method of determining the concentration of a gas component in a gas mixture comprising same, wherein the gas component is reversibly reactive with hydroxyl functionality, and said hydroxyl functionality is regenerable in the presence of water vapor to re-establish the hydroxyl functionality, the method comprising the steps of:
(a) providing a quartz crystal microbalance including a quartz crystal with a surface functionalized with hydroxyl functionality which reversibly reacts with the gas component to yield a surface-bound reaction product that (1) effects a change in the oscillation frequency of the quartz crystal and (2) subsequent to reaction is regenerable in the presence of water vapor to re-establish the hydroxyl functionality on said surface; and
(b) sensing the oscillation frequency of the quartz crystal and generating an output correlative of the concentration of the gas component in the gas stream;
(c) subsequent to the sensing of the oscillation frequency of the quartz crystal, regenerating the surface bearing the bound reaction product by exposure to ambient air with relative humidity, to repopulate the quartz crystal surface with —OH functionality, by reaction of the bound reaction product with atmospheric moisture.

43. A method according to claim 42, wherein the regeneration of the quartz crystal is carried out in situ, between periods of generating set output correlative of the concentration of the gas component in the gas stream, to reconstitute the surface for determining the concentration of the gas component in the gas mixture comprising same.

44. A method of determining the concentration of a gas component in a gas mixture comprising same, wherein the gas component is reversibly reactive with hydroxyl functionality, and said hydroxyl functionality is regenerable in the presence of water vapor to re-establish the hydroxyl functionality, the method comprising the steps of:
(a) providing a quartz crystal microbalance including a quartz crystal with a surface functionalized with hydroxyl functionality which reversibly reacts with the gas component to yield a surface-bound reaction product that (1) effects a change in the oscillation frequency of the quartz crystal and (2) subsequent to reaction is regenerable in the presence of water vapor to re-establish the hydroxyl functionality on said surface; and
(b) sensing the oscillation frequency of the quartz crystal and generating an output correlative of the concentration of the gas component in the gas stream;
wherein the gas component in the gas mixture comprising same, is selected from the group consisting of trichlorosilane, trimethylindium, dimethylaluminumhydroxide, tetrachlorotitanium, tetrakisdiethylamidotitanium, tetrakisdimethylamidotitanium, tetraethylorthosilicate, tungsten, hexafluoride, copper hexafluoroacetylacetonate, vinyl trimethylsilane, pentakisdiethylamidotantalum, dimethylamidotantalum, fluorinated derivatives of tetraethylorthosilicate, trimethylgallium, triethylindium, dichlorosilane, octamethylcyclotetrasiloxane, titaniumisopropoxide, iron pentacarbonyl, isopropanol and trimethylaluminum.

45. A method of determining the concentration of a gas component in a gas mixture comprising same, wherein the gas component is reversibly reactive with hydroxyl functionality, and said hydroxyl functionality is regenerable in the presence of water vapor to re-establish the hydroxyl functionality, the method comprising the steps of:
(a) providing a quartz crystal microbalance including a quartz crystal with a surface functionalized with hydroxyl functionality which reversibly reacts with the gas component to yield a surface-bound reaction product that (1) effects a change in the oscillation frequency of the quartz crystal and (2) subsequent to reaction is regenerable in the presence of water vapor to re-establish the hydroxyl functionality on said surface; and
(b) sensing the oscillation frequency of the quartz crystal and generating an output correlative of the concentration of the gas component in the gas stream;
wherein the gas component comprises a halosilane component.

46. A method of determining the concentration of a gas component in a gas mixture comprising same, wherein the gas component is reversibly reactive with hydroxyl functionality, and said hydroxyl functionality is regenerable in the presence of water vapor to re-establish the hydroxyl functionality, the method comprising the steps of:
(a) providing a quartz crystal microbalance including a quartz crystal with a surface functionalized with hydroxyl functionality which reversibly reacts with the gas component to yield a surface-bound reaction product that (1) effects a change in the oscillation frequency of the quartz crystal and (2) subsequent to reaction is regenerable in the presence of water vapor to re-establish the hydroxyl functionality on said surface; and
(b) sensing the oscillation frequency of the quartz crystal and generating an output correlative of the concentration of the gas component in the gas stream;

wherein the gas component comprises a trichlorosilane component.

47. A method of determining the concentration of a gas component in a gas mixture comprising same, wherein the gas component is reversibly reactive with hydroxyl functionality, and said hydroxyl functionality is regenerable in the presence of water vapor to re-establish the hydroxyl functionality, the method comprising the steps of:

(a) providing a quartz crystal microbalance including a quartz crystal with a surface functionalized with hydroxyl functionality which reversibly reacts with the gas component to yield a surface-bound reaction product that (1) effects a change in the oscillation frequency of the quartz crystal and (2) subsequent to reaction is regenerable in the presence of water vapor to re-establish the hydroxyl functionality on said surface; and (b) sensing the oscillation frequency of the quartz crystal and generating an output correlative of the concentration of the gas component in the gas stream;

wherein the gas component comprises a metalalkyl component.

* * * * *